(12) United States Patent
Abidov et al.

(10) Patent No.: US 6,489,326 B1
(45) Date of Patent: Dec. 3, 2002

(54) MEDICINAL PREPARATION AND PROCESS FOR MANUFACTURING THEREOF

(75) Inventors: Musa Tazhudinovich Abidov, ul. Lobachevskogo, d.94, kv.34, Moscow (RU); Alexandr Petrovich Khokhlov, Moscow (RU)

(73) Assignees: Anatoliy Ivanovich Pavlov, Yekaterinburg (RU); Musa Tazhudinovich Abidov, Moscow (RU)

( * ) Notice: Subject to any disclaimer, the term of this patent is extended or adjusted under 35 U.S.C. 154(b) by 0 days.

(21) Appl. No.: 09/979,846

(22) PCT Filed: Feb. 28, 2001

(86) PCT No.: PCT/RU01/00086

§ 371 (c)(1),
(2), (4) Date: Nov. 28, 2001

(87) PCT Pub. No.: WO01/72305

PCT Pub. Date: Oct. 4, 2001

(51) Int. Cl.$^7$ .................... C07D 237/32; A61K 31/502
(52) U.S. Cl. ........................................ 514/248; 544/237
(58) Field of Search ........................... 544/237; 514/248

(56) References Cited

U.S. PATENT DOCUMENTS 4,226,993 A * 10/1980 Buckler et al. ............. 544/237

FOREIGN PATENT DOCUMENTS

| RU | 130 903 | * | 10/1959 |
| RU | 656 516 A | * | 4/1979 |
| RU | 2 113 222 | * | 6/1998 |
| RU | 2 138 264 | * | 5/1999 |

OTHER PUBLICATIONS

M. D. Mashkovsky, *Medicinal Preparations*, Meditsina, Moscow (1985), vol. 2, p. 172.*

* cited by examiner

*Primary Examiner*—John M. Ford
(74) *Attorney, Agent, or Firm*—Kenyon & Kenyon

(57) ABSTRACT

The present invention can be used in medical practice specifically in chemical and pharmaceutical production of medicinal agents capable of modulating the immune system. This invention essentially relates to a new medicinal preparation 5-amino-2,3-dihydrophthalazine-1,4-dione sodium salt having immunomodulatory, antiinflammatory, and antioxidant properties. The preparation is obtained from 3-nitrophthalanhydride by consecutive isolation of intermediate and end products. The intermediate products include 5-nitro-2,3-dihydrophthalazine-1,4-dione and 5-amino-2,3-dihydrophthala2ine-1,4-dione. The reaction between 5-amino-2,3-dihydrophthalazine-1,4-dione and sodium hydroxide yields the target product, 5-amino-2,3-dihydrophthalazine-1,4-dione sodium salt. The method allows to produce the medicinal preparation with high pharmaceutical activity. It is provided an example of application of this preparation.

5 Claims, No Drawings

MEDICINAL PREPARATION AND PROCESS FOR MANUFACTURING THEREOF

FIELD OF THE INVENTION

The present invention relates to the field of medicine, specifically to medicinal preparations affecting the immune system, and to production of such preparations.

BACKGROUND OF THE INVENTION

It is known a medicinal preparation "sodium nucleinate"—a sodium salt of nucleic acid—which is an immunological activity preparation, a white or yellowish powder easily soluble in water with formation of opalescent solutions, stimulating migration and cooperation of T-and B-lymphocytes, enhancing phagocytic activity of macrophages, and activity of nonspecific resistance factors (M. D. Mashkovsky, Medicinal Preparations, Meditsina, Moscow (1985), Vol. 2, p. 172 [in Russian]).

Injections of this preparation cause, however, pain feeling, which necessitates treatments of patients with analgesics.

The closest art for "sodium nucleinate" is 2-amino-1,2,3,4-tetrahydrophthalazine-1,4-dione sodium salt dihydrate, used as an immunomodulator, which also has antiinflammatory and antioxidant properties (Russian Federation Patent No. 21113222, priority: Sep. 30, 1997; IPC: A 61 K 31/04, A 61 K 31/13), being a pale-yellow crystalline powder easily soluble in water.

Administration of this preparation to patients with impaired cellular immunity, e.g., in case of malignant neoplasms, activates macrophages, interleukins and other acute-phase proteins. In case of inflammatory processes this immunomodulator inactivates macrophages for several hours, but stimulates the microbicidal system in cells.

The preparation does not cause side effects and allergic reactions, however, in patients with chronic and other diseases long-term treatment with this agent causes tolerance and decreases the efficiency of therapy with this medicinal preparation, which dictates the necessity of substituting other more efficient analogues for the preparation.

It is known a method for manufacturing the medicinal preparation including obtaining 3-amino-phthalhydrazide, its molecular rearrangement, followed by treatment with sodium hydroxide, and isolation of the target product of 2-amino-1,2,3,4-tetrahydrophthalazine-1,4-dione sodium salt dihydrate (Russian Federation Patent No. 2138264, Priority; May 6, 1999; IPC: A 61 K 31/50, C 07 D 237/32, Bull. No. 27, Sep. 27, 1999).

This method allows to increase the yield of product and decrease the amount of waste products, however, its use is limited to manufacturing of said preparation.

The closest art to the present invention is the method for manufacturing 5-amino-2,3-dihydrophthalazine-1,4-dione (luminol) (see e.g., USSR Inventor's Certificate No. 130903, Priority: Nov. 21, 1959; Bull. No. 16, 1960), comprising reduction of 3-nitrophtlialic acid with hydrazine hydrate in a water medium in presence of a skeletal nickel catalyst, followed by evaporation of the solution, and its heating in presence of hydrazine hydrate and acetic acid at 120° C.

The end product of the known method is an orange-colored powder with pronounced luminescence properties, however, this compound is medically ineffective.

SUMMARY OF THE INVENTION

The object of the present invention is a medicinal preparation, whose effects is similar, but more pronounced, than those of the closest art thereof, e.g. for replacement of the known preparation in case of patient's tolerance thereto.

The present invention the "method for manufacturing the medicinal preparation" is based on development of a procedure providing production of an efficient medicinal preparation, having immunomodulatory, antiinflammatory, and antioxidant properties.

The problem was solved by a medicinal preparation 5-amino-2,3-dihydrophthalazine-1,4-dione sodium salt having immunomodulatory, antiinflammatory, and antioxidant properties.

This problem was solved by a method for manufacturing 5-amino-2,3-dihydrophthalazine-1,4-dione sodium salt, comprising reduction of the product by hydrazine hydrate in presence of a skeletal nickel catalyst, first by interacting 3-nitro-phthalanhydride with hydrazine hydrate in acetic acid at 90–120° C. with formation of 5-nitro-2,3-dihydrophthalazine-1,4-dione, after reduction thereof by hydrazine hydrate in a water-alkaline medium in presence of a skeletal nickel catalyst, isolating 5-amino-2,3-dihydrophthalazine-1,4-dione, which is then treated by sodium hydroxide in the presence of a lower alcohol or a ketone at 20–80° C. to obtain the target product.

DETAILED DESCRIPTION OF THE PREFERRED EMBODIMENT

The medicinal preparation is a white or pale-yellow crystalline powder easily soluble in water.

The medicinal preparation is obtained by the following process:

3-nitro-phthalanhydride ($C_8H_3NO_6$, 50–60 g) is mixed with acetic acid ($CH_3COOH$, 120–200 ml) and heated to 90–100° C. under mixing with dropwise admixing of hydrazine hydrate ($N_2H_4.H_2O$, 15–20 ml), maintaining temperature of the reaction mixture at 105–120° C. After addition of hydrazine hydrate, the reaction mass is boiled and held at least 20–45 min and then rapidly cooled to 70–85° C.

Crystallized 5-nitro-2,3-dihydrophthalazine-1,4-dione ($C_8H_5N_3O_4$) is filtered and washed with acetic acid and distilled water. The product (5–10 g) is additionally removed from the filter, the total yield of which comprises 80–85% per 3-nitro-phthalanhydride weight.

5-nitro-2,3-dihydrophthalazine-1,4-dione (40–50 g) and potassium hydroxide (KOH, 10–15 g) are mixed in distilled water (500–700 ml) to complete dissolution. The solution is heated to 60–75° C., hydrazine hydrate ($N_2H_4.H_2O$, 12–15 ml) and Ni-Rene catalyst (2–5 g) are to the solution. This leads to a violent reaction with self-heating and emission of nitrogen ($N_2$) and hydrogen ($H_2$).

When temperature reaches 85–95° C., the reaction mixture is cooled by adding distilled water. After 20–40 min, the additional catalyst (2–5 g) is fractionally added to the solution excluding the possibility of an extremely violent reaction. When self-heating is terminated, additional amounts (5–10 g) of the catalyst are added.

After completing the reaction, the solution is decanted from the precipitated catalyst, filtered, and 5-amino-2,3-dihydrophthalazine-1,4-dion ($C_8H_7N_3O_2$) is precipitated by acidification of the reaction mixture with an aqueous solution of hydrochloric acid (HCl) or a mixture of hydrochloric and acetic acids.

The precipitate is filtered, washed with distilled water, and dried.

The product yield per 5-nitro-2,3-dihydrophthalazine-1,4-dione weight is 82–84%.

In the final stage, 5-amino-2,3-dihydrophthalazine-1,4-dione (30–40 g) is dissolved in an aqueous solution of sodium hydroxide (10–15 g NaOH per 300–500 ml $H_2O$) at a temperature of 20–80° C. The solution is filtered, mixed with a lower alcohol (ROH. 1500–2000 ml), e.g., isopropyl alcohol (iso-$C_3H_7OH$) and held at 20–25° C. for 2–3 hours, isolating the target product ($C_8H_6N_3NaO_2$).

Other lower alcohols or a ketone can also be used.

The target product yield per 5-amino-2,3-dihydrophthalazine-1,4-dione weight is 85–90%.

The obtained medicinal preparation is characterized by informative UV spectra in the field of 220–400 nm, taken in concentration of 20 μg/ml in various solvents: water, 0.01 M solution of hydrochloric acid, 95% alcohol, and 0.1 M sodium hydroxide.

INDUSTRIAL APPLICABILITY

Clinical tests showed that administration of the medicinal preparation 5-amino-2,3-dihydrophthalazine-1,4-dione sodium salt to patients with impaired cellular immunity, e.g., in case of malignant neoplasms, causes activation of macrophages, which is evident by release by them of tumor necrosis factor (TNF), interleukins, and other acute-phase proteins. Besides this, the agent initiates specific reactions of T-lymphocytes.

In case of inflammatory diseases the medicinal preparation selectively (for 4–8 hours) inactivates macrophages, decreasing the contents of TNF and acute-phase proteins, that leads to attenuation of intoxication symptoms. At the same time 5-amino-2,3-dihydrophthalazine-1,4-dione sodium salt enhances super-oxidizing function and phagocytic activity of neutrophilic granulocytes, stimulating thus the microbicidal system in cells, and attenuating inflammation process.

These results are confirmed by laboratory analyses on patients, by blood tests, that characterize immunological parameters of the leukocytic and lymphocytic systems.

The medicinal preparation introduced into organism is practically completely eliminated therefrom with expired air and urine in 20–60 min. This preparation in a wide range of doses (20–1500 mg) does not cause side effects and allergic reactions, and its efficiency is similar or even higher than that of prior art immunomodulator, that allows to interchange these medicinal preparations during long-term therapy, in order to prevent the development of patient's tolerance.

The medicinal preparation can be used in form of powder for injections or tablets for peroral administration.

Clinical efficiency of the developed medicinal preparation is confirmed by the following observations.

EXAMPLE NO.1

Patient S. of 58 years old.

Was hospitalized on Feb. 2, 2000 with complaints of fatigability, long-continued cough, and transient fever (presumably residual symptoms after influenza she had on Jan. 15–27, 2000).

Examination of the patient revealed sub febrile temperature, dry cough, and rales in the lungs.

The patient was treated with 5-amino-2,3-dmydrophthalazine-1,4-dione sodium salt (further Tamerit).

Tamerit was injected in a single dose of 300 mg in 2 ml of distilled water for 5 days and then given perorally (powder or tablets) in a dose of 100 mg, 2 times a day, 1 hour after meals.

Three days after beginning of the therapy the state of the patient was improved, cough disappeared, and temperature returned to normal.

The patient was considered to be in a satisfactory state in 10 days after beginning of the therapy.

Results of laboratory analyses are shown in Table 1.

EXAMPLE NO.2

Patient I., 68 years old.

Was hospitalized with complaints of difficult urination and urges to urinate.

Ultrasound examination revealed hypertrophy of the prostate.

Diagnosis: stage II prostatic adenoma.

Two courses of therapy with 2-amino-1,2,3,4-tetrahydrophthalazine-1,4-dione sodium salt dihydrate were performed by injections for 20 and 15 injections, respectively, with a 30-day interval between the injections. Doses of the preparation were from 100 to 500 mg in 1–5 ml of distilled water correspondingly.

The size of adenoma decreased after the first course of 20 injections, but remained without further positive dynamic after the second course of final 15 injections.

The patient state was considered to be unstable.

The patient was additionally daily injected with Tamerit—10 injections in a single dose of 200 mg in 2 ml of distilled water, 1 injection daily.

The state of this patient was improved, urination was normalized.

The results of laboratory analyses are shown in Table 2.

EXAMPLE NO.3

Patient G., 42 years old.

Was hospitalized with diagnosis of erysipelas of the left forearm, edema, and exacerbation of psoriasis (temperature at hospitalization was 39.9° C.).

Before hospitalization, the symptoms of psoriasis were controlled by ointments.

Tameril was injected daily in a single dose of 200 mg in 2 ml water.

Edema and hyperemia of the left forelimb disappeared in 4 days after beginning of the therapy.

The patient received injections of Tamerit in a single dose of 100 mg in 1 ml water for the next 5 days.

The patient was considered to be in a satisfactory state. The state of the skin in the face and hands was improved.

The patient was prescribed to take Tamerit perorally in a single dose of 100 mg (1 tablet) 2–3 times a day for 7–10 days.

The results of the laboratory analyses are shown in Table 3.

TABLE 1

Laboratory Analyses of Patient S.

| Parameter | Before therapy | After therapy |
|---|---|---|
| Routine blood test | | |
| Hemoglobin, g/liter | 100 | 147 |
| Erythrocytes, *$10^{12}$/liter | 3.9 | 5.0 |
| Color index | 0.85 | 0.9 |

TABLE 1-continued

Laboratory Analyses of Patient S.

| Parameter | Before therapy | After therapy |
|---|---|---|
| Leukocytes, *10⁹/liter | 4.0 | 5.5 |
| Eosinophils, % | 2.9 | 3.0 |
| Neutrophils: | | |
| Stab, % | 6.0 | 6.0 |
| Segmented, % | 69.5 | 74.0 |
| Lymphocytes, % | 20.5 | 23.0 |
| Monocytes, % | 5.5 | 6.0 |
| ESR, mm/h | 5 | 13.0 |
| Biochemical blood test | | |
| Iron, mg/dl | 50.0 | 51.5 |
| Glucose, mmol/liter | 4.2 | 5.3 |
| Urea, mg/dl | 19.0 | 16.5 |
| Uric acid, mg/dl | 5.3 | 7.1 |
| Albumin, g/liter | 37.5 | 50.0 |
| Protein, g/liter | 76.5 | 71.5 |
| Cholesterol, mg/dl | 176.6 | 154.0 |
| Triglycerides, mg/dl | 212.1 | 195.0 |
| Total bilirubin, mg/dl | 0.35 | 0.4 |
| Creatinine, mg/dl | 0.6 | 0.45 |
| Alkaline pliosphatase, U/liter | 198.0 | 212.0 |
| Creatine kinase, U/liter | 32.8 | 34.0 |
| Aspartate transaminase, U/l | 33.0 | 29.5 |
| Alanine transaminase, U/liter | 85.0 | 70.7 |
| g-Glutamyltransferase, U/liter | 94.5 | 93.0 |
| Lactate dehydrogenase, U/liter | 201.0 | 207.5 |
| Cellular and humoral immunity tests | | |
| Immunoglobulin A, g/liter | 2.15 | 2.20 |
| Immunoglobulin M, g/liter | 2.0 | 2.21 |
| Immunoglobulin C, g/liter | 11.0 | 12.4 |
| T-lymphocytes, % | 52.0 | 67.0 |
| B-lymphocytes, % | 18.0 | 24.5 |
| Latex phagocytosis, % | 60.0 | 76,2 |
| TNF | 15.0 | 22.5 |
| T-helpers, % | 26.0 | 29.5 |
| T-suppressors, % | 21.0 | 23.5 |

TABLE 2

Laboratory Analyses of Patient I.

| Parameter | Before therapy | After injections 2-amino | After injections 5-amino |
|---|---|---|---|
| Routine blood test | | | |
| Hemoglobin, g/liter | 120 | 130 | 135 |
| Erythrocytes, *10¹²/liter | 5.0 | 5.20 | 5.25 |
| Color index | 0.9 | 0.95 | 0.95 |
| Leukocytes, *10⁹/liter | 6.50 | 6.20 | 6.21 |
| Eosinophils, % | 4.0 | 3.80 | 3.85 |
| Neutrophils: | | | |
| Stab, % | 6.5 | 5.5 | 6.0 |
| Segmented, % | 60.0 | 64.3 | 70.0 |
| Lymphocytes, % | 12.0 | 12.5 | 14.6 |
| Monocytes, % | 3.0 | 2.5 | 2.5 |
| ESR, mm/h | 357 | 17.0 | 10 |
| Biochemical blood test | | | |
| Iron, mg/dl | 116.4 | 122.5 | 123 |
| Glucose, mmol/liter | 5.0 | 5.4 | 6.0 |
| Urea, mg/dl | 10.1 | 16.2 | 15.9 |
| Uric acid, mg/dl | 2.7 | 5.3 | 6.3 |
| Albumin, g/liter | 38.8 | 51.6 | 60.5 |
| Protein, g/liter | 71.3 | 69.0 | 65.5 |
| Cholesterol, mg/dl | 204.2 | 195.7 | 176.4 |
| Triglycerides, mg/dl | 160.1 | 135.0 | 128.0 |
| Total bilirubin, mg/dl | 0.3 | 0.52 | 0.55 |
| Creatinine, mg/dl | 0.47 | 0.38 | 0.34 |
| Alkaline pliosphatase, U/liter | 212.7 | 202.0 | 207.2 |
| Creatine kinase, U/liter | 34.0 | 37.5 | 38.5 |
| Aspartate transaminase, U/l | 35.5 | 29.9 | 28.6 |
| Alanine transaminase, U/liter | 87.7 | 72.5 | 68.2 |
| g-Glutamyltransferase, U/liter | 105.5 | 97.5 | 92.4 |
| Lactate dehydrogenase, U/liter | 204.7 | 210.0 | 214.5 |
| Cellular and humoral immunity tests | | | |
| Immunoglobulin A, g/liter | 2.07 | 2.33 | 2.41 |
| Immunoglobulin M, g/liter | 1.92 | 2.07 | 2.11 |
| Immunoglobulin G, g/liter | 11.1 | 12.3 | 12.6 |
| T-lymphocytes, % | 54.5 | 66.0 | 71.6 |
| B-lmphocytes, % | 15.5 | 23.8 | 29.1 |
| Latex phagocytosis, % | 44.0 | 65.3 | 83.0 |
| TNF | 15.5 | 20.9 | 23.0 |
| T-helpers, % | 27.2 | 30.7 | 32.4 |
| T-suppressors, % | 19.7 | 23.5 | 24.0 |

TABLE 3

Laboratory Analyses of patient G

| Parameter | Before therapy | After therapy |
|---|---|---|
| Routine blood test | | |
| Hemoglobin, g/liter | 122 | 148 |
| Erythrocytes, *10¹²/liter | 6.2 | 6.9 |
| Color index | 0.92 | 0.98 |
| Leukocytes, *10⁹/liter | 7.0 | 6.2 |
| Eosinophils, % | 4.7 | 4.0 |
| Neutrophils: | | |
| Stab, % | 6.0 | 5.7 |
| Segmented, % | 62.0 | 65.5 |
| Lymphocytes, % | 19.9 | 26.3 |
| Monocytes, % | 2,7 | 2.0 |
| ESR, mm/h | 37 | 16.0 |
| Biochemical blood test | | |
| Iron, mg/dl | 114.4 | 125.5 |
| Glucose, mmol/liter | 5.4 | 5.9 |
| Urea, mg/dl | 12.9 | 11.9 |
| Uric acid, mg/dl | 3.2 | 4.15 |
| Albumin, g/liter | 46.5 | 57.1 |
| Protein, g/liter | 76.2 | 77.7 |
| Cholesterol, mg/dl | 209.0 | 200.6 |
| Triglycerides, mg/dl | 167.0 | 172.2 |
| Total bilirubin, mg/dl | 0.85 | 0.65 |
| Creatinine, mg/dl | 0.90 | 0.85 |
| Alkaline pliosphatase, U/liter | 209.0 | 221.0 |
| Creatine kinase, U/liter | 31.5 | 37.5 |
| Aspartate transaminase, U/l | 30.5 | 27.3 |
| Alanine transaminase, U/liter | 80.1 | 58.5 |
| g-Glutamyltransferase, U/liter | 93.1 | 95.2 |
| Lactate dehydrogenase, U/liter | 210.5 | 229.6 |
| Cellular and humoral immunity tests | | |
| Immunoglobulin A, g/liter | 2,20 | 2,47 |
| Immunoglobulin M, g/liter | 1,80 | 2,31 |
| Immunoglobulin G, g/liter | 13,0 | 13,7 |
| T-lymphocytes, % | 57,7 | 60,3 |
| B-lymphocytes, % | 26,2 | 25,0 |
| Latex phagocytosis, % | 60,6 | 83,4 |
| TNF | 16,5 | 24,4 |
| T-helpers, % | 19,0 | 31,2 |
| T-suppressors, % | 18,2 | 20,1 |

What is claimed is:

1. A method for manufacturing of 5-amino-2,3-dihydrophthalazine-1,4-dione sodium salt comprising the following steps:
   (a) interaction of 3-nitro-phmalanhydride with hydrazine hydrate in acetic acid at 90–120° C. yielding in a product of interaction;
   (b) reduction of the product of interaction formed on step (a) by hydrazine hydrate in a water-alkaline medium in presence of a skeletal nickel catalyst with forming of a reaction mixture containing 5-amino-2,3-dihydrophthalazine-1,4-dione;
   (c) isolation of 5-amino-2,3-dihydrophthalazine-1,4-dione from the reaction mixture formed on step (b);
   (d) treatment of 5-amino-2,3-dihydrophthalazine-1,4-dione at 20–80° C. by sodium hydroxide with addition of a lower alcohol or ketone with forming of a mixture containing 5-amino-2,3-dihydrophthalazine-1,4-dione sodium salt;
   (e) isolation of 5-amino-2,3-dihydrophthalazine-1,4-dione sodium salt from the mixture formed on step (d).

2. A pharmaceutical composition comprising 5-amino-2,3-dihydro phthalazine-1,4-dione sodium salt and an inert carrier.

3. A method of treating a patient in need of an immunomodulator comprising treating said patient with an effective amount of the composition of claim 2.

4. A method of treating inflammation comprising treating a patient in need of such treatment with an anti-inflammatory effective amount of a composition of claim 2.

5. A method of treating a patient in need of an anti-oxidant comprising treating said patient with an effective amount of the composition of claim 2.

* * * * *